US008889140B2

(12) United States Patent
Lee et al.

(10) Patent No.: US 8,889,140 B2
(45) Date of Patent: Nov. 18, 2014

(54) COMPOSITIONS AND METHODS FOR TISSUE REPAIR

(75) Inventors: Randall J. Lee, Hillsborough, CA (US); Shirley Mihardja, Daly City, CA (US); Manley Huang, Palo Alto, CA (US); James W. Larrick, Mountain View, CA (US)

(73) Assignees: TransTarget, Inc., Sunnyvale, CA (US); The Regents of the University of California, Oakland, CA (US)

( * ) Notice: Subject to any disclaimer, the term of this patent is extended or adjusted under 35 U.S.C. 154(b) by 521 days.

(21) Appl. No.: 12/601,522

(22) PCT Filed: May 30, 2008

(86) PCT No.: PCT/US2008/065303
§ 371 (c)(1),
(2), (4) Date: May 24, 2010

(87) PCT Pub. No.: WO2008/151005
PCT Pub. Date: Dec. 11, 2008

(65) Prior Publication Data
US 2010/0291080 A1 Nov. 18, 2010

Related U.S. Application Data

(60) Provisional application No. 60/941,051, filed on May 31, 2007.

(51) Int. Cl.
| *A61K 39/00* | (2006.01) |
| *A61K 39/44* | (2006.01) |
| *C07K 16/00* | (2006.01) |
| *C07K 14/715* | (2006.01) |
| *C07K 14/705* | (2006.01) |
| *A61K 47/48* | (2006.01) |
| *C07K 14/78* | (2006.01) |
| *C12N 9/64* | (2006.01) |
| *C07K 14/47* | (2006.01) |
| *C07K 14/52* | (2006.01) |
| *C07K 16/28* | (2006.01) |

(52) U.S. Cl.
CPC ............. *C07K 14/78* (2013.01); *C07K 14/7151* (2013.01); *C07K 14/70525* (2013.01); *C07K 14/70542* (2013.01); *A61K 47/48415* (2013.01); *A61K 47/48538* (2013.01); *C12N 9/6475* (2013.01); *C07K 2319/00* (2013.01); *C07K 14/4721* (2013.01); *C07K 14/52* (2013.01); *C07K 14/70553* (2013.01); *C07K 14/70564* (2013.01); *C07K 14/4716* (2013.01); *C07K 16/2833* (2013.01)
USPC .................. 424/184.1; 424/185.1; 424/192.1; 424/178.1; 530/391.1; 530/391.7

(58) Field of Classification Search
None
See application file for complete search history.

(56) References Cited

U.S. PATENT DOCUMENTS

| 5,780,052 A   * | 7/1998  | Khaw et al. ................... 424/450 |
| 5,840,691 A   * | 11/1998 | Furcht et al. .................. 514/9.3 |
| 7,129,052 B1 * | 10/2006 | Roberts et al. ................ 435/7.1 |
| 2003/0219752 A1* | 11/2003 | Short ................................ 435/6 |
| 2006/0002852 A1 | 1/2006  | Saltzman et al. |
| 2007/0014869 A1* | 1/2007  | Matheny ....................... 424/551 |

OTHER PUBLICATIONS

Khaw BA, Torchilin VP. Targeting in Myocardial Infarction. Methods Mol Med. 2000;25:159-191.*
Ehrhardt et al. Selectins-an emerging target for drug delivery. Adv Drug Deliv Rev. Mar. 3, 2004;56(4):527-49.*
Marks et al. Selective Apoptotic Killing of Malignant Hemopoietic Cells by Antibody-Targeted Delivery of an Amphipathic Peptide. Cancer Res Mar. 15, 2005 65; 2373-2377.*
Halin et al. Antibody-Based Targeting of Angiogenesis. News Physiol. Sci. 16: 191-194, 2001.*
Huang et al., Injectable Biopolymers Enhance Angiogenesis after Myocardial Infarction Tissue Engineering, 11(11/12): 1860-1866, 2005.*
Li et al. An All-D Amino Acid Peptide Model of R1(IV)531-543 from Type IV Collagen Binds the R3â1 Integrin and Mediates Tumor Cell Adhesion, Spreading, and Motility. Biochemistry 1997, 36, 15404-15410.*
Apple, F.S.; "Tissue specificity of cardiac troponin I, cardiac troponin T and creatine kinase-Mb"; *Clin. Chim. ACTA*; 284: 151-159 (1999).
Aversano, T. et al.; "A chimeric IgG4 monoclonal antibody directed against CD18 reduces infarct size in a primate model of myocardial ischemia and reperfusion"; *J. Am Coll. Cardiol.*; 25(3): 781-788 (1995).
Corda et al.; "Extracellular Matrix and Growth Factors During Heart Growth"; *Heart Failure Reviews*; 5: 119-130 (2000).
Gullberg, D., et al.; "Analysis of alpha 1 beta 1, alpha 2 beta 1 and alpha 3 beta 1 integrins in cell—collagen interactions: identification of conformation dependent alpha 1 beta 1 binding sites in collagen type I"; *EMBO J.*; 11(11): 3865-3873 (1992).
Gumina, R.J., et al.; "The leukocyte cell adhesion cascade and its role in myocardial ischemia-reperfusion injury"; *Basic Res. Cardiol.*; 92(4): 201-213 (1997).
Irwin, M.W., et al.; "Tissue expression and immunolocalization of tumor necrosis factor-alpha in postinfarction dysfunctional myocardium"; *Circ.*; 99(11): 1492-1498 (1999).
Jaakkola, K., et al.; "Vascular adhesion protein-1, intercellular adhesion molecule-1 and P-selectin mediate leukocyte binding to ischemic heart in humans"; *J. Am. Coll. Cardiol.*; 36(1): 122-129 (2000).
Kalawski, R., et al.; "Soluble adhesion molecules in reperfusion during coronary bypass grafting"; *Eur J. Cardiothorac. Surg.*; 14: 290-295 (1998).

(Continued)

*Primary Examiner* — Maher Haddad
(74) *Attorney, Agent, or Firm* — Kilpatrick Townsend & Stockton LLP

(57) ABSTRACT

The present invention provides compositions and methods for targeting an extracellular matrix derived (EMD) peptide predominantly to an injured tissue, as opposed to an uninjured tissue in vivo. The targeted EMD peptide facilitates the repair and/or regeneration of the injured tissue by providing a surface for cells to attach and grow, thereby facilitating the repair and/or regeneration of the injured tissue.

5 Claims, 5 Drawing Sheets

(56) References Cited

OTHER PUBLICATIONS

Ma, X.L., et al.; "Monoclonal antibody to L-selectin attenuates neutrophil accumulation and protects ischemic reperfused cat myocardium"; *Circ.*; 88(2): 649-658 (1993).

Pepper, M.S.; et al.; "Angiogenesis: a paradigm for balanced extracellular proteolysis during cell migration and morphogenesis"; *Enzyme Protein*; 49: 138-162 (1996).

Sierra, D.H.; "69.Fibrin sealant adhesive systems: a review of their chemistry, material properties and clinical applications"; *J. Biomater Appl.*; 7(4): 309-352 (1993).

Spring, et al.; "Two contrary functions of tenascin: dissection of the active sites by recombinant tenascin fragments;" *Cell*; 59: 325-334 (1989).

Sun, B., et al.; "Activation of NF κ B and Expression of ICAM-1 in Ischemic-reperfused Canine Myocardium"; *J. Mol. Cell Cardiol.*; 33(1): 109-119 (2001).

Tuckwell, et al.; "Conformation dependence of integrin-type II collagen binding. Inability of collagen peptides to support alpha 2 beta 1 binding, and mediation of adhesion to denatured collagen by a novel alpha 5 beta 1-fibronectin bridge"; *J. Cell Sci.*; 107(4): 993-1005 (1994).

Vandenberg, P., et al.; "Characterization of a type IV collagen major cell binding site with affinity to the alpha 1 beta 1 and the alpha 2 beta 1 integrins"; *J. Cell Biol.*; 113: 1475-1483 (1991).

Vogel et al.; "The tissue engineering puzzle: A molecular perspective"; *Ann. Rev. Biomed. Eng.*; 5: 441-463 (2003).

Werb, et al.; "Regulation of extracellular matrix degradation by cell-extracellular matrix interactions"; *Cell Differ. Dev.*; 32: 299-306 (1990).

Yamada, et al.; "Time course of myocardial infarction evaluated by indium-111-antimyosin monoclonal antibody scintigraphy: clinical implications and prognostic value"; *J. Nucl. Med.*; 33: 1501-1508 (1992).

* cited by examiner

CELL ATTACHMENT TO VARIOUS EMD PROTEINS OR PEPTIDES
*IN VITRO*

1A

1B

1C

CELL PROLIFERATION ON VARIOUS EMD PROTEINS OR PEPTIDES *IN VITRO*

2A

2B

2C

CELL MIGRATION ON VARIOUS EMD PROTEINS OR PEPTIDES *IN VITRO*

*IN VIVO* TARGETING OF HEP III TO INJURED MYOCARDIAL TISSUE

4A

4B

SEQUENCE LISTING

<160> NUMBER OF SEQ ID NOS: 4

<210> SEQ ID NO 1
<211> LENGTH: 13
<212> TYPE: PRT

```
<213> ORGANISM: Artificial Sequence
<220> FEATURE:
<223> OTHER INFORMATION: synthetic EMD peptide Hep I

<400> SEQUENCE: 1

Thr Ala Gly Ser Cys Leu Arg Lys Phe Ser Thr Met Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: synthetic EMD peptide Hep III

<400> SEQUENCE: 2

Gly Glu Phe Tyr Phe Asp Leu Arg Leu Lys Gly Asp Lys Tyr
1               5                   10

<210> SEQ ID NO 3
<211> LENGTH: 8
<212> TYPE: PRT
<213> ORGANISM: Artificial Sequence
<220> FEATURE:
<223> OTHER INFORMATION: synthetic EMD peptide FC/HV

<400> SEQUENCE: 3

Trp Gln Pro Pro Arg Ala Arg Ile
1               5

<210> SEQ ID NO 4
<211> LENGTH: 13
<212> TYPE: PRT
<213> ORGANISM: Artificial Sequence
<220> FEATURE:
<223> OTHER INFORMATION: synthetic EMD peptide RGD

<400> SEQUENCE: 4

Gly Arg Gly Asp Ser Pro Ala Ser Ser Pro Ile Ser Cys
1               5                   10
```

COMPOSITIONS AND METHODS FOR TISSUE REPAIR

CROSS-REFERENCES TO RELATED APPLICATIONS

This application claims benefit of U.S. Provisional Patent Application No. 60/941,051, filed on May 31, 2007, the disclosure of which is hereby incorporated by reference.

FIELD OF THE INVENTION

This invention relates to compositions and methods for the repair and/or regeneration of an injured tissue by targeting an extracellular matrix derived (EMD) peptide to the injured tissue.

BACKGROUND OF THE INVENTION

Organ or tissue failure remains a frequent, costly, and serious problem in health care despite advances in medical technology. Available treatments include organ transplantation, surgical reconstruction, mechanical devices (e.g. pace makers and kidney dialysis machines), drug therapy, and tissue engineering. These treatments, however, are not perfect solutions. Organ transplantation is limited by the availability of donors and complications such as tissue rejection. Surgical reconstruction is costly, highly invasive, and not always effective. Mechanical devices cannot functionally replace an organ, for example, dialysis machines can only help to remove some of the metabolic waste from the body. Likewise, maintaining drug concentration levels in vivo, comparable to the control systems of the body, are difficult to achieve. Finally, tissue engineering while promising, is encumbered by size limitations that typically require the assembly of the engineered tissue in vitro, followed by surgical implantation in vivo.

Recent advances in the medical, biological and physical sciences have given rise to new strategies for tissue engineering. For example, in one approach to engineering artificial skin, dermal fibroblasts are suspended in a polymer mesh, whereas another approach involves fibroblasts seeded in a collagen gel, which is then coated with a layer of human epidermal cells (see, e.g., Vogel, et al., *Ann. Rev. Biomed. Eng.* 5:441-463 (2003)). The use of extracellular matrix (ECM) molecules, such as collagen, is an area of active research in tissue engineering as a way to facilitate the regeneration or repair of damaged tissue in vivo.

Although many different compounds and cellular constituents are important for repair and regeneration of injured tissue, the ECM is of particular interest. ECM proteins play a pivotal role in cell adhesion, cell signaling, cell proliferation, and regulating tissue organization and differentiation. The main components of the ECM include structural proteins such as collagen and elastin, adhesive proteins such as laminin, fibronectin, and collagen IV, anti-adhesive proteins such as tenascin, thrombospondin, and osteopontin, and proteoglycans (see, e.g., Corda, et al., *Heart Failure Reviews* 5:119-130 (2000)). ECM molecules also have the ability to activate various intracellular signaling pathways, depending on the nature of the adhesion complex formed between the cell and the ECM protein. (see, e.g., Vogel, et al., *Ann Rev. Biomed. Eng.* 5:441-463 (2003).

Cells adhere to and interact with the ECM via specific receptors. One class of such receptors is the integrin proteins, which make up a large family of transmembrane heterodimer receptors composed of alpha and beta subunits. There are at least fourteen known alpha subunits and eight known beta subunits that associate in various combinations to form at least twenty distinct receptors. One class of integrin receptors known to interact with ECM proteins are integrins having the β1 subunit, also known as very late antigen (VLA) proteins. VLA proteins are expressed on a variety of cells and serve as receptors for many ECM proteins including collagen, fibronectin, and laminin. Binding of ECM proteins by their cognate receptor (e.g. integrin receptors) is important for both promoting stable interactions between the cells and their environment, and initiating intracellular signaling pathways for a variety of cellular processes important for tissue repair and/or regeneration. For example, ECM-integrin signaling has been shown to play a role in cell migration, cell survival, cellular proliferation, and cellular differentiation. See, Vogel et al. (2003).

The present invention fulfills a need in the area of tissue repair and regeneration that is not currently provided for in the art. In particular, the present invention provides for compositions and methods useful for the repair and regeneration of injured tissues in vivo by targeting an extracellular matrix derived (EMD) peptide to an injured tissue where the EMD peptide can provide a surface for cell attachment and growth, thereby facilitating the repair and regeneration of the injured tissue.

BRIEF SUMMARY OF THE INVENTION

The present invention provides compositions and methods for the repair and/or regeneration of an injured tissue, comprising a targeted extracellular matrix derived (EMD) peptide conjugated to an injury-associated antigen-specific binding component for the repair and/or regeneration of an injured tissue. The targeted EMD peptide can provide for a surface at the injured tissue whereby cells can attach and grow, thereby facilitating the repair of the injured tissue in vivo.

The present inventors have surprisingly discovered that EMD peptides ranging in size from about 8 amino acids to about 100 amino acids can mimic the properties of full length proteins from which the EMD peptides are derived, as described herein. These short peptides are advantageous because they are easy to manufacture, have reduced immunogenicity, lower toxicity, show greater homogeneity and reproducibility in conjugation to an injury-associated antigen-specific binding component, and are easier and more cost effective to manufacture as pharmaceutical compositions as compared to the full-length proteins or longer peptides as disclosed herein.

One aspect of the invention is a composition comprising an injury-associated antigen-specific binding component conjugated to an EMD peptide. The injury-associated antigen-specific binding component comprises a molecule that specifically binds an injury-associated antigen that is either expressed or unmasked as a result of tissue injury. The EMD peptide is a peptide or a concatamer of a peptide that ranges in length from about 8 amino acid residues to about 100 amino acid residues. The EMD peptides of the invention exhibit: i) cell attachment; ii) cell activation; and iii) chemotropic properties.

In some embodiments, the EMD peptide further exhibits a positive angiogenic property. In some embodiments, the EMD peptide is selected from the group consisting of a Hep III peptide as shown in SEQ ID NO:2, and RGD as shown in SEQ ID NO:4. In some embodiments, the EMD peptide is a concatamer of a peptide having a length from about 8 amino acids to about 100 amino acids. In some embodiments, the EMD peptide is derived from a protein selected from the group consisting of collagen, laminin, tenascin-C, fibronectin, fibrin, fibrinogen, and elastin.

In some embodiments, the injury-associated antigen is selected from the group consisting of a myosin light chain, a myosin heavy chain, a troponin I, a caspase-3, a VCAM-1, an ICAM-1, a P-selectin, an E-selectin, a L-selectin, a Mol/CD18, a TNF-α, a Tumor Necrosis Factor (TNF) receptor-1, a TNF receptor-2, a VAP-1, an annexin, an osteopontin, an osteonectin, a thrombospondin, a laminin, a fibronectin, a membrane bound stem cell factor, a hyaluron, an elastin, or a collagen molecule.

In some embodiments of the invention, the injury-associated antigen-specific binding component is an antibody. In some embodiments, the antibody is an intact antibody or a modified antibody. In some embodiments, the antibody is selected from the group consisting of: an IgG, IgM, IgD, IgE, a human antibody, a humanized antibody, a mammalian antibody, a non-human mammalian antibody, a non-mammalian antibody, and a chimeric antibody. In some embodiments the antibody is an antibody fragment. In some embodiments, the antibody fragment is selected from the group consisting of: an (Fab)'2 fragment, an Fab fragment, a scFv, a minibody, and a nanobody. In some embodiments, the injury-associated antigen-specific binding component is an antibody mimetic. In some embodiments the antibody mimetic is selected from the group consisting of: a non-antibody polypeptide, an anticalin, a polypeptide with a fibronectin type III domain and a nonglycosylated single chain polypeptide composed of two or more independent binding domains.

In some embodiments, the injury associated antigen-specific binding component and the EMD peptide are linked through recombinant or chemical means. In some embodiments, the conjugation is completed using recombinant methodologies (e.g. fusion proteins). In some embodiments, the conjugation is completed using a chemical means selected from the group consisting of: covalent bonding, disulfide bonding, hydrogen bonding, electrostatic bonding, conformational bonding, or homobifunctional or heterobifunctional cross-linkers.

In some embodiments, the injured tissue is selected from the group consisting of: cardiac, cartilage, bone, bone marrow, dental, hepatic, neural, vascular, and renal tissue. In some embodiments, the composition of the invention further comprises a pharmaceutical excipient.

Another aspect of the present invention provides a method for repairing and/or regenerating an injured tissue. The method involves administering to a subject a composition comprising an injury-associated antigen-specific binding component conjugated to an EMD peptide. The injury-associated antigen-specific binding component comprises a molecule that specifically binds an injury-associated antigen that is either expressed or unmasked as a result of tissue injury. The EMD peptide is a peptide or a concatamer of a peptide that ranges in length from about 8 amino acid residues to about 100 amino acid residues. The EMD peptides of the invention exhibit i) cell attachment; ii) cell activation; and iii) chemotropic properties.

In some embodiments, the subject is a mammal. In some embodiments, the mammal is a human.

In some embodiments, the tissue injury is selected from the group consisting of: ischemic injury, perfusion/re-perfusion injury, congestive heart failure dental decay, bone fracture, cartilage damage, inflammation, chemotherapy, radiation injury, thermal injury, and trauma. In some embodiments, the injury is an ischemic cardiovascular injury. In some embodiments, the ischemic cardiovascular injury is selected from the group consisting of: myocardial infarction, peripheral vascular disease, stroke, myocardial conduction disorder, and congestive heart failure.

In some embodiments, the route of administration of the targeted EMD peptide is via injection. In some embodiments, the route of injection is selected from the group consisting of: intravascular, intra-muscular, intra-peritoneal, intra-ocular, subcutaneous, intra articular, and direct injection into the injured tissue. In some embodiments, the route of administration is selected from the group consisting of: oral, topical, vaginal, and rectal.

Each of the embodiments of the invention as described herein can be combined with any aspect of the invention as described herein.

BRIEF DESCRIPTION OF THE DRAWINGS

FIG. 1A shows cell attachment of HUVEC cells on a substrate coated with Col IV (positive control), Hep I, or Hep III at 20, 50, and 100 μg/ml, compared to BSA at 2 mg/ml. The results show that the positive control Col IV and the Hep III peptide were significantly better at promoting cell attachment compared to the BSA control, and that the Hep I peptide was not significantly different from that of the BSA control at ($p<0.05$). These results demonstrate that the Hep III peptide exhibits a cell attachment property. FIGS. 1B and 1C show the attachment of HUVEC cells to a substrate coated with fibronectin (positive control) at 10 and 100 μg/ml, RGD peptide (FIG. 1B) or FCHV peptide (FIG. 1C) at 20, 50, and 100 μg/ml, compared to BSA control at 2 mg/ml. The results show that the positive control fibronectin and the RGD peptide were significantly better at promoting cell attachment compared to the BSA control, and that the FCHV peptide was not significantly different from that of the BSA control. These results demonstrate that the RGD peptide exhibits a cell attachment property.

FIG. 2A shows cell proliferation of HUVEC cells cultured on substrates coated with Col IV (positive control), Hep I, or Hep III at 20, 50, and 100 μg/ml compared to BSA at 2 mg/ml. The results show that the positive control Col IV, and the EMD peptides Hep I and Hep III were significantly better at promoting cell proliferation, at each concentration tested, compared to the BSA control at ($p<0.05$). These results demonstrate that both the Hep I and the Hep III EMD peptides exhibit a cell activation property as evidenced by their ability to stimulate cell proliferation in vitro. FIGS. 2B and 2C shows the proliferation of HUVEC cells on substrates coated with fibronectin (positive control) at 10 and 100 μg/ml, RGD peptide (FIG. 2B) and FCHV peptide (FIG. 2C) at 20, 50, and 100 μg/ml compared to BSA control at 2 mg/ml. The results show that the positive control fibronectin and the RGD peptide were significantly better at stimulating cellular proliferation compared to the BSA control, while the FCHV peptide was not statistically different as compared to the BSA control. These results demonstrate that the RGD peptide, but not the FCHV peptide, exhibits a cell activation property as evidenced by the ability of the RGD peptide to stimulate cell proliferation compared to BSA control.

FIG. 3A shows haptotactic migration of HUVEC cells on membranes coated with various concentrations of Col IV (positive control), Hep I, and Hep III using a modified Boyden chamber as detailed in Example 3. FIG. 3B shows the results for haptotactic migration of HUVEC cells on membranes coated with fibronectin (positive control), RGD peptide or FCHV peptide. The concentrations of protein or peptide tested were from 500 ng/ml to 300 μg/ml, and were compared to the migration on untreated membranes. The results show that the positive controls Col IV and fibronectin, as well as the EMD peptides Hep I, Hep III and RGD promoted haptotactic migration compared to that of untreated membranes at ($p<0.05$). The EMD peptide FCHV did not promote haptotactic migration of HUVEC cells compared to that of untreated membranes. These results demonstrate that the EMD peptides Hep I, Hep III, and RGD each exhibit a chemotropic property as evidenced by their ability to stimulate haptotactic migration of HUVEC cells as detailed in Example 3.

FIG. 4A shows the targeted antibody (visualized by the brown staining) in the region of the myocardial infarct. FIG. 4B is a negative control.

DETAILED DESCRIPTION OF THE INVENTION

Figure 1:
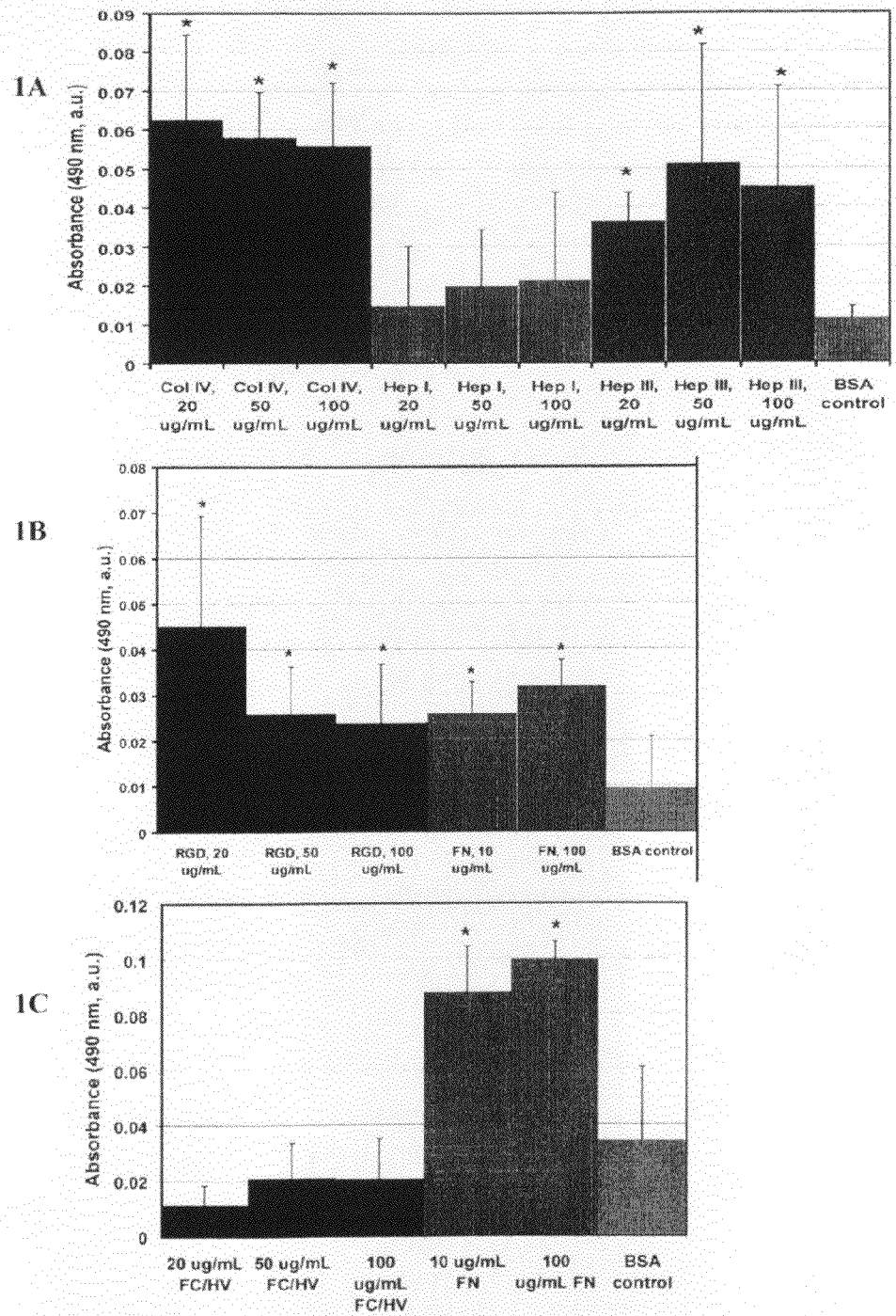
FIG. 1 shows the ability of different EMD peptides at various concentrations to promote cell attachment in vitro.

The present invention is based on the surprising discovery that an EMD peptide, having a length from about 8 amino acids to about 100 amino acids, exhibiting: i) cell attachment; ii) cell activation; and iii) chemotropic properties, conjugated to an injury-associated antigen-specific binding component can be predominantly targeted to an injured tissue as opposed to uninjured tissue in vivo for the repair and/or regeneration of the injured tissue.

I. Definitions

As used herein, the following terms have the meanings ascribed to them below unless otherwise specified.

The phrase "injured tissue" as used herein refers to any alteration in a tissue that results in the loss or damage of cells comprising that tissue, or any alteration to the tissue that results in the organ, of which the tissue is a part, performing less efficiently as compared to before the alteration. Exemplary non-limiting tissue injuries may include ischemia, perfusion/re-perfusion, cardiovascular injury, hypoxia, hypertrophy, hyperplasia, trauma, bone fracture, inflammation, dental decay, apoptosis, chemotherapy, radiation injury, thermal injury and fibrosis.

The phrase "repair of an injured tissue" as used herein refers to the process by which an EMD peptide can provide a surface for the attachment, migration, proliferation and differentiation of cells, thereby facilitating the repair and/or regeneration of the injured tissue. Non-limiting examples evidencing repair and/or regeneration of an injured tissue may include: the more rapid healing, reduced scarring or decreased fibrosis in an injured tissue treated with an EMD peptide, as compared to the healing of the injured tissue in the absence of the EMD peptide.

The term "injury-associated antigen" as used herein refers to a polypeptide, carbohydrate, or glycoprotein present on the surface of a cell in an injured tissue. The antigen may be predominantly expressed on the surface of a cell following tissue injury, or it may be an antigen that is exposed or unmasked as a result of the tissue injury. For example, injuries to the myocardium caused by ischemic heart disease can lead to exposure of cardiac antigens such as myosin light chain, myosin heavy chain, and troponin I.

The term "binding component" as used herein refers to a molecule (e.g., a polypeptide, or a nucleic acid, etc.) that specifically binds to an injury associated antigen. As used herein, the term "specifically" or "specific binding" typically means at least a 2-fold increase in binding over background, preferable greater than a 10-fold increase, and most preferred at least a 100-fold increase or greater over that of background. Specific binding between an injury associated antigen and a binding component generally means an affinity of $10^6$ $M^{-1}$ or stronger, preferable at least $10^8$ $M^{-1}$ or stronger. Specific binding between a protein binding component and an injury associated antigen can be determined using any binding assay known in the art, including but not limited to gel electrophoresis, western blot, ELISA, flow cytometry, and immunohistochemistry.

The term "polypeptide" as used herein refers to an amino acid polymer having at least two amino acid residues.

The term "antibody" refers to a polypeptide encoded by an immunoglobulin gene or functional fragments thereof that specifically binds to and recognizes an antigen (e.g., a cardiac antigen such as myosin light chain or troponin I). The antibody is comprised of at least one binding domain formed from the folding of variable domains of an antibody molecule to form three-dimensional binding spaces with an internal surface shape and charge distribution complementary to the features of an antigenic determinant of an antigen which allows an immunological reaction with the antigen. An antigenic determinant is that portion of an antigen molecule that determines the specificity of the antigen antibody reaction. Antibodies as used herein include naturally occurring as well as recombinant proteins comprising antigen specific binding domains, as well as antibody fragments including Fab, Fab', F(ab)$_2$, F(ab')$_2$ fragments, scFv, minibodies and nanobodies.

The recognized immunoglobulin genes include variable region and constant region genes. The constant region genes include kappa, lambda, alpha, gamma, delta, epsilon, and mu. Immunoglobulin light chains are classified as either kappa or lambda. Immunoglobulin heavy chains are classified as gamma, mu, alpha, delta, or epsilon, which define the immunoglobulin classes, IgG, IgM, IgA, IgD and IgE, respectively.

An exemplary immunoglobulin (whole antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100-110 or more amino acids primarily responsible for antigen recognition.

The term "antibody mimetic" refers to non-antibody molecule comprising at least one binding component that specifically binds to an antigen. Antibody mimetics are typically polypeptides or proteins comprising one or more regions that are amenable to specific or random sequence variation, such that the polypeptide or protein specifically binds to an antigen of interest (e.g. myosin light chain, or troponin I).

The term "extracellular matrix derived (EMD) peptide" or "EMD peptide" as used herein, refers to an amino acid polymer having between about 8 and about 100 amino acid residues, derived from an extracellular matrix protein. Non-limiting exemplary extracellular matrix proteins that can be used to derive an EMD peptide for use with the invention may include fibrinogen, fibrin, fibronectin, collagen (types I, II, III and IV), laminin, tenascin, elastin osteonectin, and osteopontin. In some embodiments, a peptide as used in the invention may have about 8, 9, 10, 12, 14, 16, 18, 20, 25, 30, 35, 40, 45, 50, 55, 60, 65, 70, 75, 80, 85, 90, 95, or about 100 amino acid residues.

The EMD peptide can be a naturally occurring fragment or cleavage product of an extracellular matrix protein, or it may be a peptide resulting from enzymatic digestion of a peptide using proteases such as trypsin. An EMD peptide can also be a recombinantly synthesized peptide corresponding to a portion of a naturally occurring extracellular matrix protein. EMD peptides suitable for use with the present invention can also have conservative variations or substitutions compared to that of the wild-type protein from which the peptide is derived. Conservative substitution tables providing functionally similar amino acids are well known in the art. Such conservatively modified variants are in addition to and do not exclude polymorphic variants, interspecies homologs, and alleles. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "cell attachment" or "attach cells" refers to the ability of an EMD peptide to support the adherence of a cell to a surface coated with the EMD peptide. Cell attachment can occur through an interaction of the EMD peptide with a receptor expressed by the cell, (e.g., integrin receptors). Cell attachment property of an EMD peptide can be shown by any suitable assay known in the art. Cell attachment property of an EMD peptide can be demonstrated by showing that cells will adhere with a detectably greater level to a surface coated with an EMD peptide as compared to surface coated with a control protein (e.g., BSA). An exemplary test that can be used to determine if an EMD peptide exhibits cell attachment property is detailed in Example 1.

The term "cell activation property" or "activate cells" refers to the ability of an EMD peptide to stimulate cellular proliferation. Any test suitable for detecting an increase in cellular proliferation of a cell contacted with an EMD peptide as compared to the cell proliferation in the absence of the peptide, or in the presence of a control protein (e.g. BSA) can be used to determine if an EMD peptide exhibits cell activation property. An exemplary test for determining is an EMD peptide exhibits cell activation property is detailed in Example 2.

The term "chemotropic property" as used herein refers to the property of an EMD peptide to support the migration of a cell over a surface coated with the EMD peptide. Chemotropic property of an EMD can be demonstrated using any test suitable in the art to demonstrate that a cell migrates over a surface coated with the EMD peptide as compared to an untreated surface. An exemplary test to determine if an EMD peptide exhibits chemotropic property is detailed in Example 3.

The term "angiogenic property" refers to the ability of an EMD peptide to stimulate angiogenesis in an injured tissue. Angiogenesis can be measured as an increase in the vascular area of an injured tissue contacted with an EMD peptide, compared to the vascular area in an injured tissue not contacted with the EMD peptide. A procedure suitable for determining whether an EMD peptide exhibits an angiogenic property is detailed in Example 5.

The term "linked" or "conjugated" as used in the present invention refers to the linkage between the injury-associated antigen-specific binding component and an EMD peptide. The linkage may be introduced through either recombinant (e.g. recombinant fusion proteins) or chemical means. Non-limiting examples of suitable chemical means include covalent bonding, disulfide bonding, hydrogen bonding, electrostatic bonding, and conformational bonding and may involve the use of homobifunctional or heterobifunctional cross linkers. Suitable cross-linking and conjugation methods are disclosed in U.S. Pat. No. 6,642,363 and U.S. Pat. Pub. No. 20060002852.

The term "therapeutically effective dose" as used herein to refers to an amount of a targeted EMD peptide sufficient to effectuate a desired result, or an amount of targeted EMD peptide required to facilitate the repair and/or regeneration of an injured tissue in vivo. Such an amount will vary depending on the effect to be achieved. The therapeutically effective dose will depend on a variety of factors, including the type of injury, the type of tissue, the extent of injury, the particular EMD peptide, and the degree of repair and/or regeneration sought as an end-point.

II. Targeted Emd Peptides for Tissue Repair and Regeneration

The invention discloses compositions and methods for targeted repair and/or regeneration of an injured tissue. As described in more detail below, the invention is an EMD peptide conjugated to an injury-associated antigen-specific binding component that targets the EMD peptide to an injured tissue. The invention is useful for the repair and/or regeneration of injured mammalian tissue in vivo. Non-limiting exemplary tissue injuries suitable for treatment with the present invention may include ischemic injury, re-perfusion injury, congestive heart failure, bone fractures, dental decay, inflammatory injury (e.g., due to placement of pace maker electrodes, or arthritis), chemotherapy, radiation or thermal injury, acute injuries resulting from trauma (e.g. vascular damage due to stents and catheters), tissue hypertrophy, tissue hyperplasia, and fibrosis. Non-limiting exemplary tissues that can be targeted with the compositions and methods described herein may include: cardiac, neural, hepatic, renal, cartilage, vascular, dental, bone, and bone marrow tissues. Non-limiting exemplary injury-associated antigens suitable for use with the invention may include: myosin light chain, myosin heavy chain, troponin I, caspases, VCAM-1, ICAM-1, P-selectin, E-selectin, L-selectin, Mol/CD18, Tumor Necrosis Factor (TNF) receptor-1, TNF receptor-2, lectin-like oxidized low-density lipoprotein receptor-1 (LOX-1), VAP-1, annexin, osteopontin, thrombospondin, laminin, fibronectin, fibrinogen, fibrin, elastin, membrane bound stem cell factor, and collagen. The injury-associated antigen-specific binding component, as described in more detail below, may be an antibody or antibody mimetic that specifically binds to an injury-associated antigen with an affinity of $10^{-6}$ M or stronger. Non-limiting exemplary binding components suitable for use with the present invention may include: antibodies, antibody fragments (e.g. Fab, Fab', F(ab)2 fragments, scFv, minibodies and nanobodies), and antibody mimetics.

As described in more detail below, an EMD peptide suitable for use with the present invention exhibits: (i) cell attachment, (ii) cell activation, and (iii) chemotropic properties. Although many wild-type intact extracellular matrix proteins may meet these requirements, the present inventors have surprisingly discovered peptides ranging in size from about 8 amino acid residues to about 100 amino acid residues are preferred to longer peptides of whole proteins. In particular, peptides in this size range that exhibit these three requirements are easy to manufacture, have reduced immunogenicity, lower toxicity, and show greater homogeneity and reproducibility in conjugation to an injury-associated antigen-specific binding component. Further, the targeted EMD peptides of the present invention are easier and more cost effective to manufacture as pharmaceutical compositions compared to longer peptides of full-length proteins. Non-limiting exemplary EMD peptides suitable for use with the present invention may be derived from full-length proteins including: fibrinogen, fibrin, fibronectin, collagen (types I, II, III, and IV), tenascin-C, laminin, and elastin. These and other aspects of the invention are described in more detail below, and in the examples.

A. Injury Associated Antigen-Specific Binding Component

The injury-associated antigen-specific binding component specifically binds an injury-associated antigen that is either expressed or unmasked as a result of a tissue injury. Therefore, in making the composition of the invention, an injury-associated antigen must be identified.

An injury-associated antigen can be any molecule expressed on the surface of a cell in an injured tissue, or an antigen that is unmasked, or exposed, as a result of a tissue injury. The antigen may be a carbohydrate, protein, polypeptide, nucleic acid, lipid, proteoglycan, or any other molecule that is predominantly expressed or exposed in a tissue following injury.

Many injury-associated antigens are predominantly expressed following tissue injury. Alternatively, an antigen may be exposed or unmasked following tissue injury. For example, basement membrane antigens (e.g. laminin, fibronectin, or collagen type IV) are frequently exposed following vascular injury as a result of stenting procedures or percutaneous transluminating coronary angioplasty (PTCA).

Non-limiting exemplary injury-associated antigens that are predominantly expressed following vascular or cardiac injury include: myosin heavy chain, myosin light chain (Yamada, et al., *J. Nuc. Med.* 33:1501-1508 (1992)) and troponin I (Apple, F. S., et al., *Clin. Chim. ACTA* 284:151-159 (1999)); vascular cell adhesion molecule (VCAM-1) (Kalawski, R., et al., *Eur J. Cardiothorac. Surg.* 14:290-295 (1998), Oguchi, et al., *Arterial Thromb Vasc. Biol.* 20:1729-1736 (2000)); intercellular adhesion molecule (ICAM-1) (Sun, B., et al., *J. Mol. Cell. Cardiol*, 33:109-119 (2001)); α4β1 integrin (Lumsen, et al., *J Vasc Surg* 26:87-93 (2000)); Mol/CD18 (Aversano, T. et al., *J. Am. Coll. Cardiol.* 25:781-788 (19995)); TNF receptor-1 and TNF receptor-2 (Irwin, M. W., et al., *Circ.* 99:1492-1498 (1999)); vascular adhesion protein-1 (VAP-1) (Jaakkola, K., et al., *J. Am. Coll. Cardiol.* 36:122-129 (2000)); and angiotensin receptors, which are expressed locally but under a different temporal sequence following myocardial injury (Yang, B., et al., *Vasc. Med.* 3:121-130 (1998)). Additional vascular antigens suitable for use with the instant invention are members of the selectin family, which are cell-surface carbohydrate-binding proteins expressed by endothelial cells and cells of the immune system. Selectins mediate a variety of transient, $Ca^{2+}$ specific cell-cell adhesion interactions with integrins. (See, e.g., Alberts, et al., MOLECULAR BIOLOGY OF THE CELL, 4th ed. (2002) Garlund Science, NY, N.Y.) Non-limiting exemplary selectin antigens suitable for use with the present invention may include: L-selectin, P-selectin (Gumina, R. J., et al., *Basic Res. Cardiol.* 92:201-213 (1997)); and E-selectin (Ma, X. L., et al., *Circ.* 88:649-658 (1993)).

Non-limiting exemplary antigens suitable for use with the present invention that are exposed or expressed as a result of an inflammatory response may include: Mol/CD18, TNF receptor-1, TNF receptor-2, Vascular adhesion protein-1 (VAP-1), and annexin. In some embodiments, where the inflammation at the affected site persists, released cytokines, such as IL-1 and TNF, will activate endothelial cells to express other injury-associated antigens suitable for use with the present invention, including: integrin receptors, VCAM-1, ICAM-1, E-selectin, and L-selectin.

Non-limiting exemplary antigens that are expressed or exposed following injury to bone tissue that are suitable for use with the present invention may include: osteopontin, thrombospondin, and tenascin-C.

Non-limiting exemplary antigens that are expressed or exposed following injury to cartilage tissue that are suitable for use with the present invention may include: collagen (e.g., types I, II, III and IV), glycosaminoglycans (e.g., chondroitin sulfate), and inflammatory markers (such as Mol/CD18, TNF receptor-1, and TNF receptor-2).

Non-limiting exemplary antigens that are expressed or exposed following injury to hepatic or renal tissues can include: antigens associated with an inflammatory response as discussed herein and apoptotic markers such as caspase-3. Additional injury-associated antigens suitable for use with the present invention will be well known to persons of skill in the art.

1. Antigen-Specific Binding Component

Another component of the present invention is a binding component specific to the injury-associated antigen. Binding components suitable for use with the present invention are well known in the art. Non-limiting exemplary binding components suitable for use with the present invention may include: an antibody (monoclonal or polyclonal), an antibody fragment, a single chain variable fragment (scFv), and an antibody mimetic. Binding components suitable for use with the present invention can be either generated using methods well known in the art, or purchased from commercial suppliers. Binding components purchased from commercial suppliers (e.g. antibodies) can be modified, for example, to generate antibody fragments (e.g. Fab, $F(ab')_2$, scFv). Antibody mimetics, as described in more detail below, are non-antibody molecules. Non-limiting exemplary antibody mimetics suitable for use with the invention may include: anticalins, polypeptides with fibronectin type III domains, avimers, adnectins, and non-glycosylated single chain polypeptides having two or more binding domains.

a) Antibodies

Methods of producing monoclonal or polyclonal antibodies that react specifically with antigens expressed on cells of injured tissues are well known to those of skill in the art. For example, preparation of monoclonal antibodies by immunizing mice with an appropriate immunogen is described in, e.g., Coligan, *Current Protocols in Immunology* (1991): Harlow & Lane, ANTIBODIES, A LABORATORY MANUAL, Cold Spring harbor Publication, New York (1988); Goding, *Monoclonal Antibodies: Principles and Practice* (2d ed. 1986); Kohler & Milstein, *Nature* 256:495497 (1975). Antibody preparation by selection of antibodies from libraries of nucleic acids encoding recombinant antibodies packaged in phage or similar vectors is described in, e.g., Huse, et al., *Science* 246:1275-1281 (1989) and Ward, et al., *Nature* 341: 544-546 (1989). In addition, antibodies can be produced recombinantly using methods known in the art and described in e.g., Sambrook, et al., Molecular Cloning, A laboratory Manual (2nd ed. 1989); Kriegler, Gene Transfer and Expression: A Laboratory Manual (1990); and Current Protocols in Molecular Biology (Ausubel et al., eds., 1994).

The production of monoclonal antibodies is well known in the art. In general, spleen cells from an animal immunized with the desired immunogen (e.g., a myosin light chain, myosin heavy chain, or troponin I) are immortalized, commonly by fusion with a myeloma cell (see, Kohler & Milstein, *Eur. J. Immunol.* 6:511-519 (1976). Colonies arising from single immortalized cells are screened for the production of antibodies having the desired binding specificity and binding affinity for the particular antigen. In some embodiments, the immunized animal is a transgenic animal that expresses human immunoglobulin genes for the production of human antibodies, as disclosed in U.S. Pat. No. 6,833,268. In some embodiments, the production of human or humanized antibodies is carried out as described in U.S. Pat. No. 6,673,986, or using methods known to a person of ordinary skill in the art.

In some embodiments, the genes encoding the heavy and light chain immunoglobulins can be cloned from a hybridoma cell that produces a desired monoclonal antibody specific for a particular injury associated antigen. In some embodiments, gene libraries encoding heavy and light chains of monoclonal antibodies are generated. In some embodiments, random combinations of the heavy and light chain gene products are used to generate a pool of antibodies with differing antigenic specificities (see, e.g., Kuby, Immunology ($3^{rd}$ ed. 1997)). Nucleic acids encoding antibodies that specifically bind to an injury associated antigen can be isolated directly from mRNA, cDNA, or DNA libraries using methods well known in the art, such as polymerase chain reaction (PCR) and ligase chain reaction (LCR) (see, e.g., U.S. Pat. Nos. 4,683,195 and 4,683,202; PCR Protocols: A Guide to Methods and Applications (Innis et al., eds, 1990)). Phage display technology can be used to identify antibodies and Fab fragments that specifically bind to selected antigens (see, e.g., McCafferty et al., Nature 348:552-554 (1990); Marks et al., Biotechnology 10:779-783 (1992)).

In addition to the antibodies generated using the methods well known in the art, or described herein, antibodies specific for injury-associated antigens suitable for use with the present invention can be purchased from commercial sources. For example, antibodies against myosin light chain and troponin-I can be purchased from: Abcam Ltd., (Cambridge, U.K.); Accurate Chemical & Scientific Corporation (Westbury, N.Y.) and Beckman Coulter (Fullerton, Calif.). Antibodies against activated caspase 3, fibronectin, collagen (Types I, IV, and VII), laminin, TNF-α, TNF receptors-1 and -2, are available from Research Diagnostics (Concord, Mass.). VCAM-1 antibodies are available from BioSource International (Carmillo, Calif.). ICAM-1 antibodies are available from AbCam Ltd. (Cambrige, U.K.). Osteopontin antibodies are available from Sigma-Aldrich (St. Louis, Mo.). Thrombospondin, Tenascin-C, and selectin antibodies are available from Chcmicon, (Temecula, Calif.). These and other commercially available antibodies are suitable for use with the present invention.

(1) Modification of Antibodies

Once an antibody of appropriate specificity and affinity has been obtained, the antibody can be conjugated to an EMD peptide, or the antibody can be modified prior to conjugation. Suitable modifications of the antibodies include, generation of antibody fragments or humanizing, primatizing, or chimerizing the antibody.

Antibody fragments suitable for use with the present invention include any antibody fragment capable of specifically binding to the specific injury-associated antigen and capable of being conjugated to an EMD peptide. Non-limiting exemplary antibody fragments may include: F(ab')$_2$, Fab, Fv, single chain Fv (scFv), dsFv, $V_L$ and $V_H$ (see, e.g., Fundamental Immunology (Paul ed., 4d ed. 1999); Bird, et al., Science 242:423 (1988); and Huston, et al., Proc. Natl. Acad. Sci. USA 85:5879 (1988)). The antibody fragments can be obtained by a variety of methods, including, digestion of an intact antibody with an enzyme, such as pepsin (to generate (Fab')$_2$ fragments) or papain (to generate Fab fragments); or de novo synthesis. Antibody fragments can also be synthesized using recombinant DNA methodology. In some embodiments F(ab')$_2$ fragments that specifically bind myosin light chain, myosin heavy chain, or troponin-I are generated.

As mentioned above, humanized antibodies may be generated for use as an injury-associated antigen-specific binding component. Humanized antibodies are antibodies in which the antigen binding loops, i.e., CDRs, obtained from the $V_H$ and $V_L$ regions of a non-human antibody are grafted to a human framework sequence. Methods for humanizing or primatizing non-human antibodies are well known in the art. Generally, a humanized antibody has one or more amino acid residues introduced into it from a source, which is non-human. Humanization, i.e., substitution of non-human CDRs or CDR sequences for the corresponding sequences of a human antibody, can be performed following the methods described in, e.g., U.S. Pat. Nos. 5,545,806; 5,569,825; 5,633,425; 5,661,016; Riechmann et al., Nature 332:323-327 (1988); Marks et al., Bio/Technology 10:779-783 (1992); Morrison, Nature 368:812-13 (1994); Fishwild et al., Nature Biotechnology 14:845-51 (1996). Transgenic mice, or other organisms such as other mammals, may also be used to express humanized or human antibodies, as disclosed in U.S. Pat. No. 6,673,986.

b) Antibody Mimetics

In some embodiments, antibody mimetics are used as the injury associated antigen specific binding component. Antibody mimetics use non-immunoglobulin protein scaffolds as alternative protein frameworks for the variable regions of antibodies. As defined herein, antibody mimetics are polypeptides comprising one or more regions (i.e., loop regions) that are amenable to specific or random sequence variation such that the antibody mimetic specifically binds to an antigen of interest (e.g., an injury associated antigen such as myosin light chain). Non-limiting exemplary antibody mimetics can include anticalins which are based on lipocalins and are described in Weiss and Lowman, Chem. Biol., 7(8): 177-184 (2000); Skerra, J. Biotechnol. 74(4):257-275; and WO99/16873; polypeptides with a fibronectin type III domain and at least one randomized loop as described in e.g., WO01/64942 and U.S. Pat. No. 6,818,418; polypeptides with a P-sandwich structure as described in e.g. WO 00/60070; and non-glycosylated single chain polypeptides composed of two or more monomer domains, that can separately bind any type of target molecule including proteins, joined by a linker, as described in U.S. patent application Ser. Nos. 10/133,128 and 10/871,602.

The antibody mimetics having monomer domains of non-glycosylated single chain polypeptides described in U.S. patent application Ser. Nos. 10/133,128 and 10/871,602 are distinct from the complementarity-determining region (CDR) of an antibody. The antibody mimetic polypeptides are able to fold independently, form stable structures, and are heat stable unlike an antibody. For example, the polypeptides are stable to 95° C. for at least 10 minutes without an appreciable loss in binding affinity. Additional characteristics of the monomer domains includes low immunogenicity, low toxicity, small size sufficient to penetrate skin or other tissues, and a range of in vivo half-life and stability.

Antibody mimetics may be generated to bind an injury-associated antigen, such as those described herein. For example, an antibody that binds a specific injury-associated antigen can be analyzed using methods known in the art, such as three-dimensional crystal structure analysis of the antibody-antigen interaction, to identify the specific residues that are critical for antigen binding. Once these residues have been identified, the loop regions of the antibody mimetics can be subjected to site directed mutagenesis such that the loop forms a binding pocket for the particular injury associated antigen. Such modifications are described in, e.g., Vogt and Skerra, *Chembiochem.* 5(2):191-9 (2004).

Lipovsek et al. (U.S. Pat. Nos. 6,818,418 and 7,115,396) discloses an antibody mimetic featuring a fibronectin or fibronectin-like scaffold and at least one variable loop. Known as Adnectins, these fibronectin-based antibody mimetics exhibit many of the same desirable characteristics of natural or engineered antibodies, including high affinity and specificity for a targeted ligand. Further, these fibronectin-based antibody mimetics exhibit certain benefits over antibodies and antibody fragments. For example, these antibody mimetics do not rely on disulfide bonds for native folding and stability, and are therefore stable under conditions that would normally breakdown antibodies.

Beste et al. (*Proc. Natl. Acad. Sci. U.S.A.* (1999) 96(5): 1898-1903) discloses an antibody mimetic based on a lipocalin scaffold (ANTICALIN™). Lipocalins are composed of a b-barrel with four hypervariable loops at the terminus of the protein. Beste (1999), subjected the loops to random mutagenesis and selected from binding with, for example, fluorescein. Three variants exhibited specific binding with fluorescein, with one variant showing binding similar to that of an anti-fluorescein antibody. Further analysis revealed that all of the randomized positions are variable, indicating that ANTICALIN™ would be suitable for use as an alternative to an antibody. ANTICALIN™ are small single chain polypeptides, typically between 160 and 180 residues in length, which provides several advantages over antibodies, including decreased cost of production, increased stability during storage, and decreased immunological reaction.

Hamilton et al. (U.S. Pat. No. 5,770,380) discloses a synthetic antibody mimetic using the rigid, non-peptide organic scaffold of calixarene, attached with multiple variable peptide loops as binding sites. The peptide loops all project from the same side geometrically from the calixarene, with respect to each other. Because of this geometric confirmation, all of the loops are available for binding, thereby increasing the binding affinity to the ligand. In comparison, however, to the other antibody mimetics, the calixarene-based antibody mimetic does not consist exclusively of polypeptide, and is therefore less susceptible to attack by protease enzymes, is relatively stable in extreme environmental conditions and has a long life-span. Further, due to the relatively small size of the antibody mimetic, it is less likely to produce an immunogenic response.

Murali et al. (*Cell. Mol. Biol.* (2003) 49(2):209-216) discloses a methodology for reducing antibodies into smaller peptidomimetics, termed "antibody-like binding peptidomimetics" (ABiP) which may also be used as an alternative to antibodies with the present invention.

Silverman et al. (*Nat. Biotechnol.* (2005) 23:1556-1561) discloses fusion proteins that are single chain polypeptides comprising multiple domains, termed "avimers." Developed from human extracellular receptor domains by in vitro exon shuffling and phage display, the avimers are a class of binding proteins somewhat similar to antibodies in their affinities and specificities for target molecules. These resulting multi-domain proteins may exhibit improved affinity (sub-nanomolar in some cases) and specificity compared to single epitope binding proteins. Additional details concerning the construction and use of avimers can be found in U.S. Pat. Pub. Nos: 20040175756, 20050048512, 20050053973, 20050089932, and 20050221384.

In addition to non-immunoglobulin protein frameworks, antibody properties have also been mimicked in compounds comprising RNA molecules and unnatural oligomers (e.g., protease inhibitors, benzodiazepines, purine derivatives and bb-turn mimics) all of which are suitable for use with the present invention as injury-associated antigen-specific binding components.

B. EMD Peptide

An EMD peptide suitable for use with the present invention has a length of about 8 amino acid residues to about 100 amino acid residues and exhibits positive: i) cell attachment; ii) cell activation; and iii) chemotropic properties. In some embodiments, the EMD peptides further exhibit a positive angiogenic property. As described in more detail below, the present inventors have surprisingly shown that while full length proteins from which an EMD peptide can be derived may exhibit cell attachment, cell activation, and chemotropic properties, not all EMD peptides derived from these proteins exhibit these properties. For example, of the four EMD peptides tested in the Examples (SEQ ID NOs: 1-4), only Hep III (SEQ ID NO:2) and RGD (SEQ ID NO:4) exhibited all three of the required properties.

Non-limiting exemplary extracellular matrix proteins suitable for deriving an EMD peptide for use with the present invention may include: fibrinogen, fibronectin, fibrin, collagen (Types I, II, III, and IV), laminin, elastin, and tenascin-c.

Any method known in the art suitable for use with the present invention may be used to derive an EMD peptide from a naturally occurring extracellular matrix protein. In some embodiments, the protein, or longer polypeptides may be enzymatically cleaved using a protease, such as trypsin. In some embodiments, EMD peptides may be identified using bioinformatic analysis and the identified peptide then produced through recombinant means. In some embodiments, an EMD peptide of the invention is a variant or a mutant of a peptide corresponding to the naturally occurring wild-type protein. In some embodiments, conservative substitutions are made to the naturally occurring protein or peptide, to improve the functional characteristics of the EMD peptide. Natural matrix polymers suitable for deriving an EMD peptide for use with the instant invention can be purified from donor sources, or purchased from commercial suppliers, for example, Sigma-Aldrich (St. Louis, Mo.) and Abnova Corp. (Taipei, Taiwan).

In some embodiments, an EMD peptide of the invention is derived from a collagen protein. The collagen family contains approximately 20 types of triple helical fibrous proteins, and constitutes approximately one-third of the total proteins in our body. Collagen provides structural integrity by resisting mechanical loading forces and degradation. Type I collagen is prevalent in a variety of tissue types including bone, skin and various internal organs and promotes cell growth and differentiation via binding of $\alpha 1\beta 1$ and $\alpha 2\beta 1$ integrins (Gullberg, D., et al., *EMBO J.* 11:3865-3873 (1992)). Type II collagen is present in cartilage and binds to chondrocytes through the $\alpha 2\beta 1$ integrin (Tuckwell, et al., *J. Cell Sci* 107(4)993-1005 (1994)). Type IV collagen is a component of the basal lamina and binds cells through the $\alpha 1\beta 1$ and $\alpha 2\beta 1$ integrins (Vandenberg, P., et al., *J. Cell Biol.* 113:1475-1483 (1991)). Non-limiting exemplary EMD peptides derived from collagen may include: Hep I, having the amino acid sequence TAGSCLRKFSTMY-OH (SEQ ID NO:1) and Hep III, having the amino acid sequence GEFYFDLRLKGDKY-OH (SEQ ID NO:2). As shown in the examples, Hep III exhibits i) cell attachment, ii) cell activation, and iii) cell migration properties, and is therefore suitable for use with the present invention. As shown in example 5, the Hep III peptide also exhibits angiogenic property. In contrast to Hep III, the Hep I peptide (as shown in SEQ ID NO:1) does not exhibit a cell attachment property, and therefore is not suitable for use with the present invention. This surprisingly shows that not all peptides derived from an extracellular matrix molecule are suitable for use with the present invention.

In some embodiments, an EMD peptide of the invention is derived from an elastin protein. Elastin is a principal component of the basal lamina and the ECM. Elastin polypeptide chains are cross-linked together to form rubber like, elastic fibers. Each elastin molecule uncoils into a more extended conformation when the fiber is stretched and will recoil spontaneously as soon as the stretching force is relaxed. Elastin combines with collagen to give tissue its shape, rigidity, and flexibility.

In some embodiments, an EMD peptide of the invention is derived from fibrinogen, an FDA-approved commercially available biological sealant and adhesive that acts as a provisional material for cellular in growth during wound repair. Fibrinogen is formed by the polymerization of fibrin monomers and is resorbed by degradation via a fibrinolytic enzyme such as plasmin (see, Pepper, M. S., et al., *Enzyme Protein* 49:138-(1996)). Fibrin contains the arg-gly-asp (RGD) motif that binds to the $\alpha 5\beta 1$ and $\alpha 8\beta 1$ integrin receptors (Sierra, D. H., *J. Biomater Appl* 7:309-(1993)).

In some embodiments, an EMD peptide of the invention is derived from a laminin protein. Laminin is a large flexible protein composed of three very long polypeptide chains arranged in the shape of an asymmetric cross and held together by disulfide bonds. Several isoforms of each type of chain can associate in different combinations to form a large family of laminin proteins that are useful in deriving and EMD peptide for use with the present invention. Laminin, like type IV collagen, can self-assemble into felt-like sheets and binds cells through $\alpha 6\beta 1$ and $\alpha 7\beta 1$ integrin receptors.

In some embodiments, an EMD peptide for use with the present invention is derived from a fibronectin protein. Fibronectin, is a large glycoprotein dimer composed of two very large subunits joined at one end by a disulfide bond. Each subunit folds into a series of functionally distinct domains, separated by regions of flexible polypeptide chain. Among the functional domains contained within fibronectin molecule are a self-association domain, collagen binding domain, heparin binding domain and a cell binding domain. A central feature of the cell binding domain is the RGD binding motif, which provides sites for cell attachment via the $\alpha 5\beta 1$ and $\alpha 8\beta 1$ integrin receptors. Non-limiting exemplary EMD peptides derived from fibronectin may include FC/HV having the amino acid sequence WQPPRARI-OH (SEQ ID NO:3) and RGD having the amino acid sequence GRGDSPASSPISC-OH (SEQ ID NO:4). As shown in the examples, RGD (SEQ ID NO:4) exhibits i) cell attachment, ii) cell activation, and iii) cell migration properties, and is therefore suitable for use with the present invention. In contrast to the RGD EMD peptide, the FC/HV peptide (as shown in SEQ ID NO:3) does not exhibit cell attachment, cell activation, or chemotropic properties, and therefore is not suitable for use with the present invention. As with the Hep I and Hep III peptides discussed above, the results from the FC/HV and RGD peptides also surprisingly demonstrate that not all peptides derived from an extracellular matrix molecule are suitable for use with the present invention.

In some embodiments, an EMD peptide for use with the present invention may be derived from a tenascin protein. Tenascin is comprised of multiple repeats of short amino acid sequences that form functional domains. Tenascin may be adhesive or non-adhesive, depending on the cell type (Spring, et al., *Cell* 59:325-334 (1989)). Tenascin is known to interact with the $\alpha 8\beta 1$ and $\alpha 9\beta 1$ integrins. Tenascin is also known to stimulate the synthesis and secretion of proteases, which may be important in cell migration and remodeling of tissue during repair and regeneration (Werb, et al., *Cell Differ. Dev.* 32:299-306 (1990)).

a) Cell Attachment Assay

EMD peptides suitable for use with the present invention must exhibit a cell attachment property as described herein. A cell attachment property refers to the adherence or attachment of cells to a substrate coated with the EMD peptide of interest.

For purposes of the present invention, an EMD peptide is deemed to exhibit cell attachment property when the percent of cells that adhere to a substrate coated with an EMD peptide of interest following a short incubation period (for example 30 minutes) is statistically greater ($p<0.05$) than the percentage of cells that adhere to a substrate in the absence of the EMD peptide. The percentage of cells that adhere to the substrate following the short incubation period can be determined using any suitable means known in the art. Non-limiting exemplary means include DNA quantitation, microscopic examination of stained cells, enzymatic analysis, and the like. Suitable cell types can include epithelial and endothelial cells. In a preferred embodiment, HUVEC cells are used. Additional cell lines suitable for use in the cell activation assays disclosed herein are well known to persons of skill in the art, as long as the results obtained with the chosen cell line are consistent with results obtained using HUVEC cells as shown in Example 1. Cell culture substrates suitable for use with the assay may be any substrate that can be coated with the EMD peptide and upon which cells can be cultured. Suitable substrates may include glass slides, plastic treated or untreated cell culture dishes, cytodex beads, or any other suitable cell culture substrate known to persons of skill in the art. An exemplary assay for determining if an EMD peptide exhibits cell attachment property is detailed in Example 1.

b) Cell Activation Assay

An EMD peptide suitable for use with the present invention must exhibit cell activation property as described herein. A cell activation property refers to cellular events that occur when a cell is activated, such as proliferation, changes in ion permeability, induction of intracellular proteins, or an increase in phosphorylation of intracellular proteins.

For purposes of the present invention, an EMD peptide is deemed to exhibit cell activation properties when a cell cultured on a substrate coated with an EMD peptide, or contacted with an EMD peptide, shows a statistically detectable increase ($p<0.05$) in cellular proliferation as compared to the proliferation rate of the cells either cultured on a substrate in the absence of the EMD peptide or cultured on a substrate in the absence of the EMD peptide.

In some embodiments, cell activation is measured as an increase in proliferation rate of cells cultured on a substrate coated with an EMD peptide of interest as compared to the proliferation rates of cells cultured on an untreated substrate in the absence of the EMD peptide. In some embodiments, parallel cultures are grown on the same substrate, and then one of the cultures is then contacted with the EMD peptide of interest, and the proliferation rate of the two cultures are then compared. The cell culture substrate may be any substrate that can be coated with the EMD peptide or any substrate on which cells can be cultured, and may include glass slides, plastic treated or untreated cell culture dishes, cytodex beads, or any other suitable substrate known to persons of skill in the art. In some embodiments, the cells used for determining cell proliferation are epithelial cells or human umbilical vascular endothelial cells (HUVEC). Additional cell lines suitable for use in the cell activation assays disclosed herein are well known to persons of skill in the art, as long as the results obtained with the chosen cell line are consistent with results obtained using HUVEC cells as shown in Example 2. In some embodiments, the method for measuring the cell proliferation is quantitating the amount of DNA, use for antibodies such as PCNA for measuring cell proliferation, 3H-thymidine, BrdU, flow cytometry, or any other method known to persons of skill in the art for measuring the rate of cell proliferation in vitro. An exemplary method for determining the rate of cell proliferation is detailed in Example 2.

c) Chemotropic Assay

EMD peptides suitable for use with the present invention must exhibit a chemotropic property as described herein. For purposes of the present invention, an EMD peptide is deemed to exhibit chemotropic property, if a cell (e.g. HUVEC) shows a statistically detectable increase ($p<0.05$) in migration on a surface coated with the EMD protein as compared to cell migration on an untreated surface.

In some embodiments, a chemotropic assay as described herein uses a modified Boyden chamber as described in Example 3. Cell types suitable for use in a chemotropic assay for determining if an EMD peptide exhibits a chemotropic property as described herein can include epithelial and endothelial cells. In a preferred embodiment, HUVEC cells are used. Additional cell lines suitable for use in the chemotropic assays disclosed herein are well known to persons of skill in the art, as long as the results obtained with the chosen cell line are consistent with results obtained using HUVEC cells as shown in Example 3. Quantification of the migrated cells can be measured using any means known in the art, for example, direct cell counts, DNA quantitation, enzymatic quantitation, and spectrophotometric determination. In a preferred embodiment, the cells on the substrate are stained and counted under a microscope. An exemplary chemotropic assay is detailed in Example 3.

d) Angiogenic Assay

In some embodiments, an EMD peptide suitable for use with the invention exhibits an angiogenic property. For purposes of the present invention, an EMD peptide is deemed to exhibit an angiogenic property when an injured tissue contacted with the EMD peptide of interest shows a statistically detectable increase ($p<0.05$) in vascular area of the injured tissue as compared to a control. A suitable assay for determining if an EMD peptide of interest exhibits an angiogenic property as described herein is detailed in Example 5.

C. Conjugation of Binding Component and Therapeutic Moiety

Once an injury-associated antigen-specific binding component and an EMD peptide have been generated, they are conjugated to form a targeted EMD peptide, as described herein. Methods for conjugating an injury-associated antigen-specific binding component to an EMD peptide are well known in the art and may include recombinant and chemical conjugation methods.

Chemical conjugation techniques suitable for use with the present invention include conjugation of functional chemical groups as described in U.S. Pat. App. No. 20060002852. Chemical group conjugation typically involves the presence of a functional chemical group on both the binding component and on the EMD peptide. Exemplary functional groups include carboxylic acids, aldehydes, amines, sulfhydrals, and hydroxyl groups. The functional groups may be conjugated by direct crosslinking using homo- or hetero-bifunctional crosslinkers. A crosslinker suitable for use with the present invention is any crosslinker that couples the binding component to an EMD peptide via a chemical modification. Non-limiting exemplary crosslinkers suitable for use in the present invention include CDI, EDC, and glutaraldehyde.

In some embodiments, the functional groups on the binding component and the EMD peptide are identical, and may be conjugated in a one-step chemical cross-linking procedure using a homobifunctional linker. Exemplary homobifunctional cross-linkers may include amine reactive cross-linkers; amine reactive cross-linkers with PEO/PEG spacers; 1,5-difluoro-2,4-dinitrobenzene (DFDNB) (useful for cross-linking between small spatial distances); sulfhydral reactive linkers (maleimides react with —SH groups at pH 6.5-7.5, forming stable thioether linkages); and sulfhydral reactive linkers with PEO/PEG spacers. In some embodiments, heterobifunctional cross-linkers will be used to join two or more different functional groups allowing for sequential conjugations with specific functional groups of proteins while minimizing undesirable polymerization or self-conjugation.

In some embodiments, the conjugation method involves the activation of hydroxyl groups, on either the EMD peptide or the binding component, with the agent, carhonyldiimidazole (CDI) in aprotic solvents (e.g., DMSO, acetone, or THF). Activation with CDI forms an imidazoyl carbamate complex with the hydroxyl group, which may then be displaced by binding the free amino group on the second component. The reaction is an N-nucleophilic substitution, which results in a stable N-alkylcarbamate linkage of the binding component to the EMD peptide. The coupling of the binding component to the EMD peptide is optimal in the pH range of 9-10 and normally requires at least 24 hours. The resulting linkage is stable and resists hydrolysis for extended periods of time.

In some embodiments, the coupling method involves the use of 1-ethyl-3-(3-dimethylaminopropyl) carbodiimide hydrochloride (EDC) or "water soluble CDI" in conjunction with N-hydroxylsulfosuccinimide (sulfo NHS) to couple the exposed carboxyl group of one component to free amino groups present on the second component in a totally aqueous environment at a physiological pH of 7.0. Briefly, the EDC and sulfo-NHS in the reaction increases the efficiency of the EDC coupling by a factor of ten-fold and provides for exceptionally gentle conditions that ensure the viability of the resultant targeted EMD peptide.

Using either of the above protocols (CDI or EDC) it is possible to activate almost any EMD peptide containing a carboxyl or hydroxyl group in a suitable solvent system that will not degrade the EMD peptide.

In some embodiments, where the EMD peptide and the binding component have free hydroxyl and carboxyl groups are conjugated using the crosslinking agent divinylsulfone. This method is particularly useful for attaching sugars or other hydroxylic compounds with bioadhesive properties to other hydroxylic compounds. Briefly, the activation involves the reaction of divinylsulfone to the hydroxyl groups on one of the components, forming vinylsulfonyl ethyl ether of the component. The vinyl groups will couple to alcohols, phenols, and even amines on the second component. Activation and coupling take place at pH 11. The linkage is then stable through the pH range from about 1 to about 8.

In some embodiments, coupling between the binding component and the EMD peptide is of a direct or indirect covalent nature. For example, the coupling may be through a linker bound to one component, or alternatively through an interaction between two molecules such as streptavidin and biotin. The coupling interaction may also be an electrostatic attraction. For example, the interaction between the binding component and the EMD peptide may be mediated by a positively charged molecule, such as polyethylencimine or poly-lysine, present on one component and a negatively charged molecule present on the other component. In some embodiments, the binding component may be conjugated to the EMD peptide by means of UV cross-linking.

In some embodiments, the binding component and the EMD peptide may be conjugated by recombinant means generating a DNA construct encoding the binding component fused to the EMD peptide. The DNA construct can then be expressed in an appropriate protein expression system, such as a prokaryotic or eukaryotic expression system well known to persons of skill in the art.

D. Pharmaceutical Formulation of a Targeted EMD Peptide

A targeted EMD peptide, comprising an injury-associated antigen-specific binding component conjugated to an EMD peptide, as described herein, can be formulated as a pharmaceutical composition for use in the methods of the present invention. General details on the techniques for formulation and administration of pharmaceutical compositions are well known in the art. See, e.g., "REMINGTON'S PHARMACEUTICAL SCIENCES", Maack Publishing Co., Easton, Pa.

In some embodiments, a pharmaceutical formulation of the invention comprises a solution of the composition and an aqueous pharmaceutically acceptable carrier. A variety of aqueous carriers can be used, e.g., buffered saline and the like. These solutions are sterile and generally free of undesirable matter. The pharmaceutical formulation may also contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the targeted EMD peptide in the formulation can vary widely, and will be selected primarily based on fluid volumes, viscosities, body weight, composition of the targeted EMD peptide, target tissue, nature of the injury, and the like in accordance with the particular mode of administration selected and the patient's needs.

In some embodiments, the pH of the pharmaceutical formulation is in the range of pH 5 to 9.5, preferably pH 6.5 to 7.5. In some embodiments, the pharmaceutical formulation comprises a suitable pharmaceutically acceptable buffer such as phosphate, tris (hydroxymethyl) aminomethane-HCl or citrate and the like. Buffer concentrations should be in the range of 1 to 100 mM. In some embodiments, the pharmaceutical formulation comprises a salt, such as sodium chloride or potassium chloride in a concentration of 50 to 150 mM. In some embodiments, the pharmaceutical formulation comprises an effective amount of a stabilizing agent such as albumin, a globulin, a detergent, a gelatin, a protamine or a salt of protamine.

In some embodiments, the pharmaceutical formulation is in the form of a sterile injectable preparation, such as sterile injectable aqueous or oleaginous suspension. The suspension may be formulated according to methods well known in the art using suitable dispersing or wetting agents and suspending agents. The sterile injectable preparation may be a sterile injectable solution or suspension in a nontoxic parenterally-acceptable diluent or solvent. Non-limiting exemplary vehicles and solvents suitable for use with the invention include: water, Ringer's solution, and an isotonic sodium chloride solution. In some embodiments, sterile fixed oils may be used as a solvent or suspending medium. For this purpose, any bland fixed oil can be employed including synthetic mono- or diglycerides, and fatty acids such as oleic acid may be used in the preparation of injectables.

III. Administration and Dosing

The compositions described herein (i.e., a targeted EMD peptide comprising an injury-associated antigen-specific binding component coupled to an EMD peptide) can be administered to a patient alone, or in conjunction with other therapies suitable for treatment of the particular injury. For example, a targeted EMD peptide may be administered in conjunction with angioplasty to facilitate the repair of injured cardiac tissue. In some embodiments, the targeted EMD peptide may be administered prior to the angioplasty, contemporaneous with the angioplasty, or subsequent to the angioplasty.

The targeted EMD peptides of the present invention may be administered by any suitable means known in the art. In some embodiments, the compositions are suitable for parenteral administration (e.g., intravenous, intramuscular, or intraperitoneal injection). The compositions of the invention may also be administered subcutaneously, into vascular spaces, or into joints, e.g., intra-articular injection. Additional routes of administration suitable for use with the present invention include intranasal, topical, vaginal, rectal, intrathecal, intra-arterial, and intraocular routes, or direct injection or application to the injured tissue. Intravascular administration is preferred.

The amount of targeted EMD peptide required to facilitate tissue repair and/or regeneration is defined as a "therapeutically effective dose." The dosage schedule and amounts effective for a particular use, i.e., the "dosing regimen," will depend upon a variety of factors, including the tissue being treated, the type of injury, the composition of the targeted EMD peptide, pharmacokinetics of the composition including bioavailability and clearance rates, the patients physical status, the route of administration, and the desired end-point sought to be achieved shall all be taken into account. Single or multiple administrations of the compositions may be administered depending on the dosage and frequency as required and tolerated by the patient. Typically, a pharmaceutical composition of the invention is administered as a single, or multiple therapeutically effective dose over a single day, several days, or weeks by daily or weekly intravenous infusion. In some cases of chronic injury, such as intractable angina, multiple doses separated by months may be required due to the changing (worsening) pathophysiological state. In any event, dosage and administration schedule should provide for a sufficient quantity of targeted EMD peptide to effectively treat the patient.

In some embodiments, a therapeutically effective dose of a targeted EMD peptide may be in a range from about 0.05 µg to about 500 µg, or about 5 µg to about 400 µg, or about 10 µg to about 300 µg, or about 25 µg to about 250 µg, or about 40 µg to about 100 µg, or about 50 µg of targeted EMD peptide per dose. In some embodiments, the amount of targeted EMD peptide is administered based on body weight. In some embodiments, the amount of targeted EMD peptide administered is from about 0.05 ng to about 500 ng, or about 5 ng to about 400 ng, or about 10 ng to about 300 ng, or about 25 ng to about 250 ng, or about 40 ng to about 100 ng, or about 50 ng of targeted EMD peptide per kg of body weight. In some embodiments, the dose is based on patient surface area. For example, in some embodiments, a targeted EMD peptide may be administered in a dose range from about 50 mg to about 400 mg/m$^2$ of surface area, or about 100 mg to about 300 mg/m$^2$ of surface area, or about 150 mg to about 250 mg/m$^2$ of surface area. In some embodiments, the dose administered is about 250 mg/m$^2$ of surface area. In some embodiments, the dose is administered as a single cycle, while in other embodiments, multiple cycles are administered. The exact dose and schedule of administration will depend on a variety of factors as discussed herein, and is well within the skill of medical professional treating the patient.

EXAMPLES

The following examples are included for illustration purposes only, and are not intended as a limitation on the invention in any way. It should be appreciated by those of skill in the art that the techniques disclosed in the examples which follow represent techniques discovered by the inventor to function well in the practice of the invention, and can thus be considered to represent preferred modes for practice of the invention. However, those skilled in the art should, in light of the present disclosure, appreciate that many changes can be made in the specific embodiments disclosed and still obtain similar results without departing from the spirit or scope of the invention.

Example 1

Cell Attachment Assay

Reagents

Immulon 1B, untreated 96-well plates (CoStar), and untreated 35 mm dishes (CoStar) were purchased from Fisher Scientific (Pittsburg, Pa.). Human umbilical vein endothelial cells (HUVECs), cell culture media and supplements were purchased from Lonza (Basel, Switzerland). EMD peptides as shown in SEQ ID Nos: 1-4, were synthesized by Commonwealth Biotechnologies Inc., (Richmond, Va.). Amino acid analysis was performed on the peptides to verify the amino acid sequence.

Cell Attachment Assay

For the adhesion studies 96-well Immulon 1B plates were used. Various concentrations of the EMD peptides (SEQ ID Nos: 1-4) were tested for their ability to bind cells, and compared to the full-length protein, from which the EMD peptides were derived as positive controls. Bovine Serum Albumin (BSA) treated wells were used as a negative control. Full-length collagen IV, and the EMD peptides Hep I, Hep III, FCHV, and RGD were tested at concentrations of 20 µg/ml, 50 µg/ml, and 100 µg/ml. Full length fibronectin was tested at concentrations of 10 µg/ml and 100 µg/ml. Negative control wells were coated with BSA at a concentration of 2 mg/ml. Fifty µL of protein or EMD peptide solutions at the various concentrations was added separate wells and incubated at 37° C. for at least 18 hours. The protein or peptide solution was then removed and the wells were blocked for 2 hours at 37° C. with 2 mg/mL BSA solution. Following the blocking procedure, wells were washed twice with PBS. HUVEC cells (Lonza, Basel Switzerland) were then added to the wells at a concentration of $5 \times 10^3$ to $1 \times 10^4$ cells per well. Following a thirty-minute incubation, cell adhesion was assessed after 30 minute incubation wells were washed and cell adhesion was determined using an MTS (3-(4,5-dimethylthiazol-2-yl)-5-(3-carboxymethoxyphenyl)-2-(4-sulfophenyl)-2H-tetrazolium, inner salt) tetrazolium/formazan assay (Promega, Madison, Wis.) according to the manufacturer's instructions.

As shown in FIG. 1, HUVEC cells in the wells coated with either the full-length proteins Col. IV and Fibronectin, or the EMD peptides Hep III (SEQ ID NO:2) and RGD (SEQ ID NO:4) showed increased cell attachment compared to cell attachment in wells coated with BSA. Notably, cell attachment in wells coated with the EMD peptides Hep I (SEQ ID NO:1) and FCHV (SEQ ID NO:3) were not statistically different from that of the BSA treated wells. See, FIG. 1. The results indicate that both the Hep III (SEQ ID NO:2) and RGD (SEQ ID NO:4) peptides exhibit cell attachment property.

Example 2

Cell Proliferation Assay

To determine if EMD peptides can activate cells by stimulating cellular proliferation, 96-well plates coated using the same protocol as described above for the cell attachment assay was used. Following treatment of the wells, HUVEC cells (Lonza, Basel Switzerland) were then added to the wells at a concentration of $5 \times 10^3$ to $1 \times 10^4$ cells per well and incubated under standard culture conditions for 1, 2, 3 or 4 days. Cell proliferation was then determined at the end of the incubation period using an MTS tetrazolium/formazan assay (Promega, Madison, Wis.) according to the manufacturer's instructions.

Figure 2:
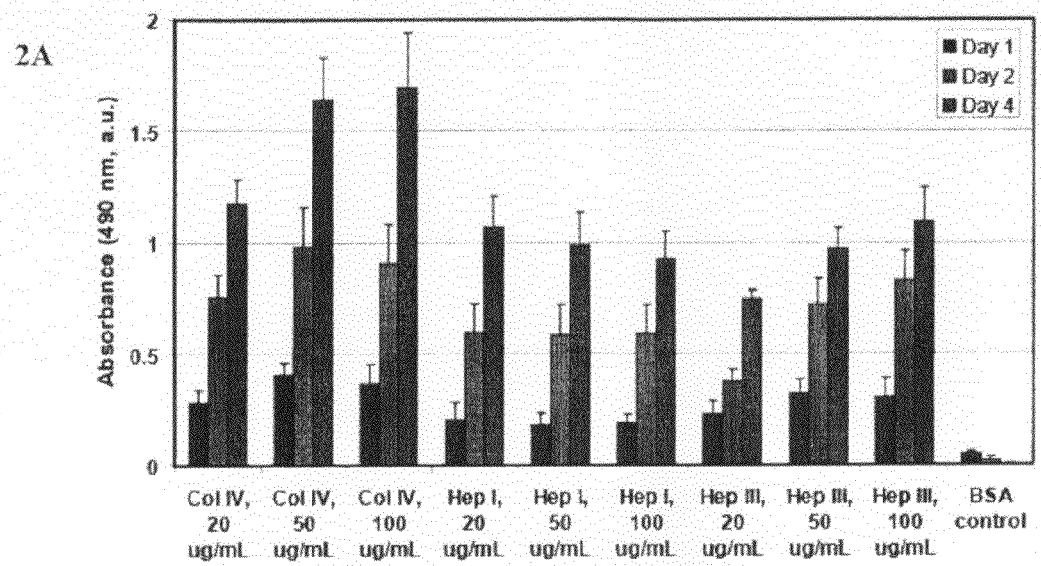
FIG. 2 shows the ability of different EMD peptides at various concentrations to activate cells by stimulating the proliferation of cells in vitro.
Figure 2:
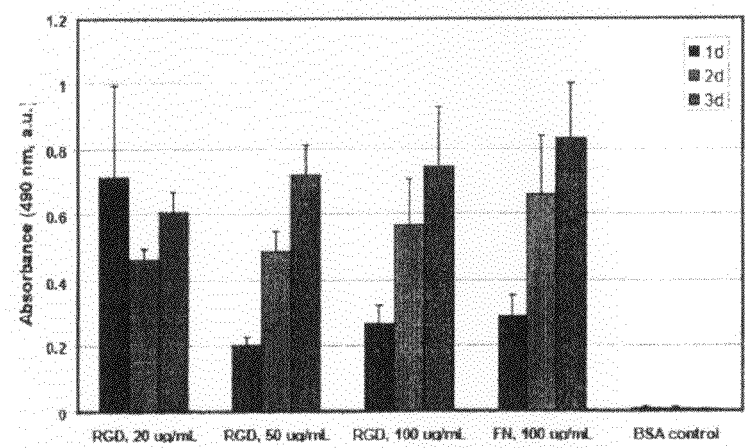
Figure 2:
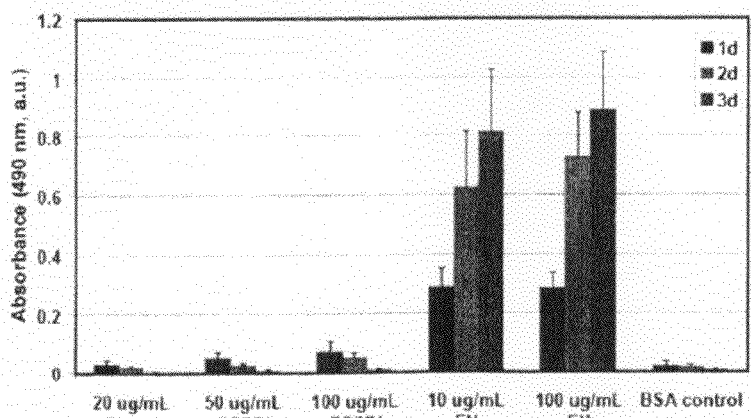

As shown in FIG. 2, full length proteins Col IV and fibronectin and EMD peptides Hep I, (SEQ ID NO:1) Hep III (SEQ ID NO:2), and RGD (SEQ ID NO:4) all showed increased cellular proliferation compared to cells cultured in wells coated with BSA. Notably, cells cultured in wells coated with FCHV (SEQ ID NO:3) was not different from that of cells cultured in wells coated with BSA. The data indicates that full length proteins Col IV and fibronectin, as well as the EMD peptides Hep I, Hep III, and RGD all exhibit cell activation property as demonstrated by increased proliferation. See, FIG. 2.

Example 3

Cell Migration Assay

In order to test the ability of EMD peptides to recruit cells haptotactic migration assays with Hep I (SEQ ID NO:1), Hep ITT (SEQ TD NO:2), FC/HV (SEQ ID NO:3), RGD (SEQ ID NO:4), FN, and Col IV were conducted using a modified Boyden chamber. Haptotactic migration was performed in triplicate and was assessed using a modified Boyden chamber (Corning, CoStar, Acton, Mass.). The assay was carried out as follows: the lower chamber was first blocked with 10% BSA for at least 30 minutes at 37° C. followed by 3 washings with PBS. The lower surface of the membrane on the upper chamber was coated with approximately 10 µL of protein or EMD peptide solution having a concentration between 500 ng/mL-300 µg/mL and allowed to incubate for 15-30 minutes at 37° C. and then allowed to air dry at room temperature under aseptic conditions. At least one assay was performed for each concentration. Basal cell media supplemented with 0.5% BSA was then added to the lower chamber and 100 µL of H U V ECs ($1 \times 10^4$ to $2 \times 10^4$ cells) in the same cell media was added to the upper chamber. The chambers were then incubated at 37° C., 5.0% $CO_2$ for 6 hours. Upon completion of the incubation period, the cells on the membrane of the upper chamber were fixed with 4% paraformaldehyde followed by removal of the cells on the upper side of the membrane with a Q-tip. Next, the membrane was carefully removed from the chamber, dipped in a 1:4000 dilution of Hoechst 33342 (Invitrogen, Carlsbad, Calif.) and placed on a glass slide. Using a fluorescent microscope (Nikon Eclipse E800) at 10× magnification, five random fields of view were photographed on each membrane for determination of the area cell density.

Figure 3:
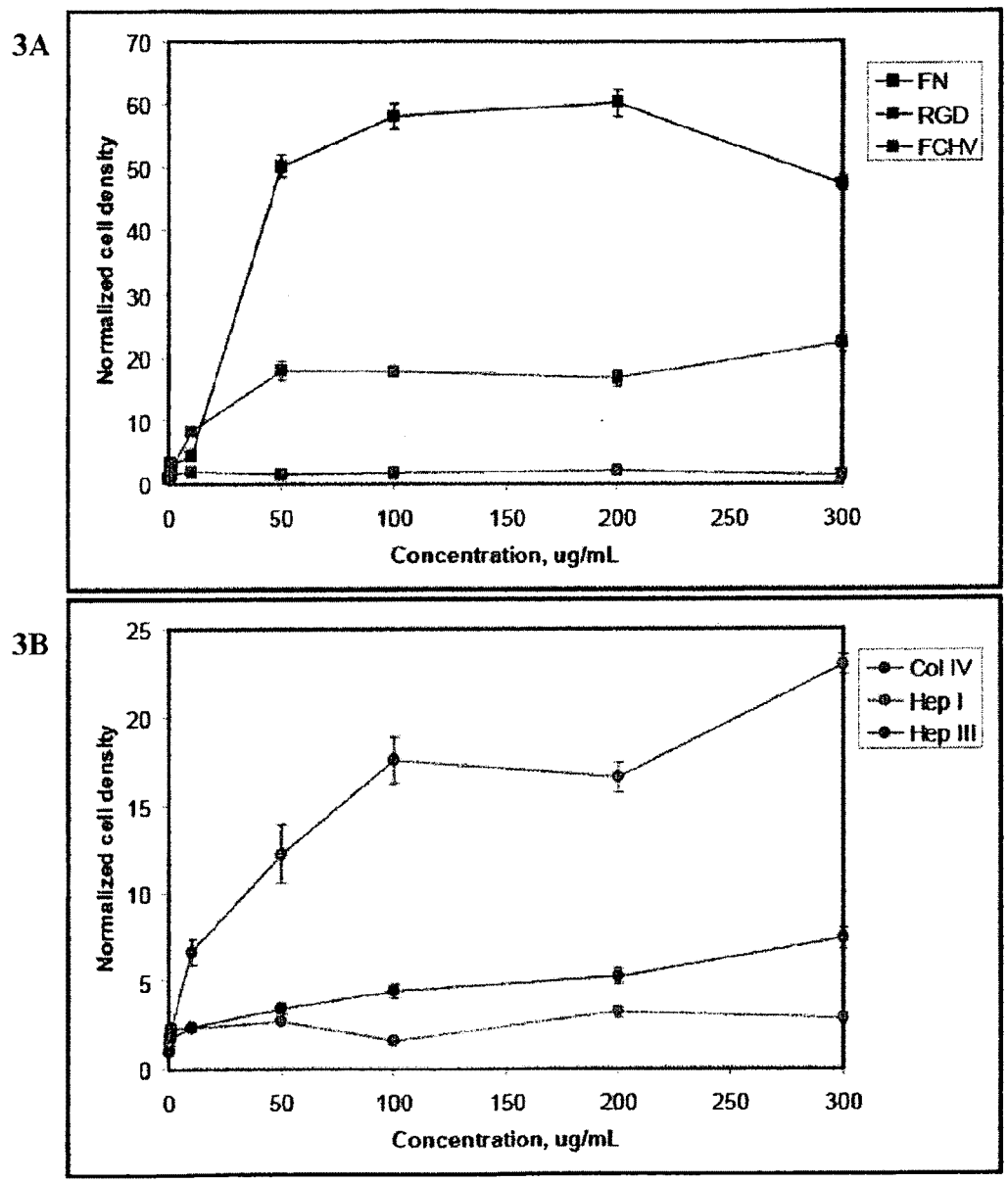
FIG. 3 shows the chemotropic property of different EMD peptides to promote haptotactic migration of HUVEC cells in vitro.

In order to allow for direct comparison, the area cell density of migrated cells was normalized to the area cell density of migrated cells on the uncoated (0 µg/mL) control membrane. See, FIG. 3. The results show that the proteins fibronectin and Collagen IV both promoted migration. Similarly, the EMD peptides Hep III (SEQ ID NO:2) and RGD (SEQ ID NO:4) also showed significant migration compared to control. Hep I (SEQ ID NO:1) showed statistically significant migration at concentrations greater than 1 μg/ml, while cells on FC/HV (SEQ ID NO:3) coated membranes did not show statistically significant migration at any of the concentrations tested compared to control membranes.

Example 4

Conjugation of a Hep III EMD Peptide to a Myosin Heavy Chain (MHC) Antibody and Targeting of the EMD Peptide to Injured Myocardium In Vivo This example demonstrates an exemplary conjugation method for linking the EMD peptide to an injury associated antigen specific binding component using carboiimide chemistry. A mouse anti-rat cardiac myosin heavy chain (anti-MHC) monoclonal antibody, was isolated from a hybridoma, ATCC deposit # HB-276, (Manassas, Va.) by Panorama Research Inc., Mountain View, Calif. For conjugating the Hep III peptide (SEQ ID NO:2) to the MHC antibody, the crosslinker 1-ethyl-3-[3-dimethylaminopropyl]carbodiimide hydrochloride (EDC, Pierce, Rockford IL.) was used. The EDC together with sulfo-NHS was incubated with the Hep III peptide followed by incubation with the MHC antibody. Unconjugated Hep III peptide was removed from the MHC-HepIII solution using a size exclusion column. In order to maximize the conjugation of the EMD peptide to the antibody, a molar excess of the peptide was used. Assessment of the conjugation efficiency can be monitored using fluorescence spectrophotometry for the EDC conjugation, where the peptide is fluorescently labeled with fluorescein. Alternatively, verification of the conjugation can be confirmed via mass spectrometry and amino acid analysis.

Figure 4:
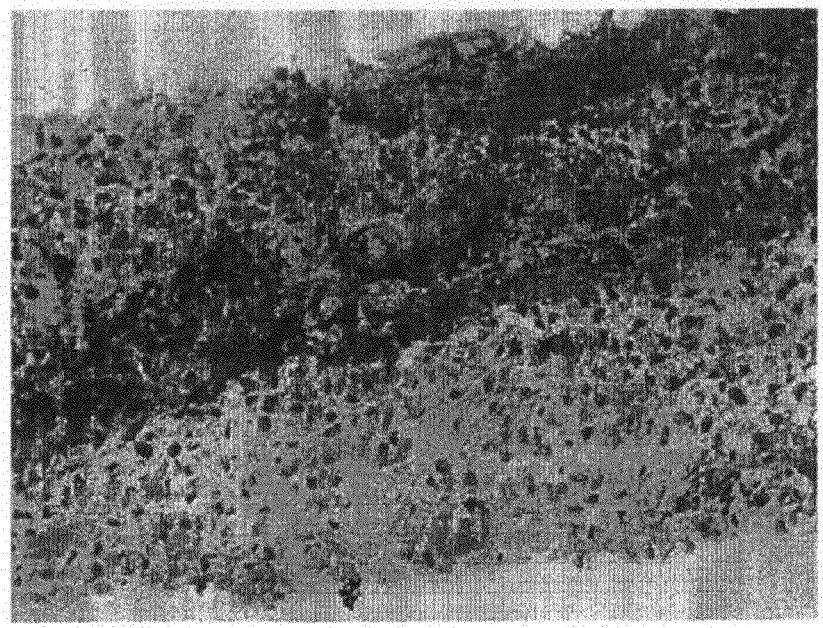
FIG. 4 illustrates the successful targeting of the EMD peptide Hep III conjugated to an anti-myosin heavy chain antibody to injured myocardial tissue in vivo.
Figure 4:
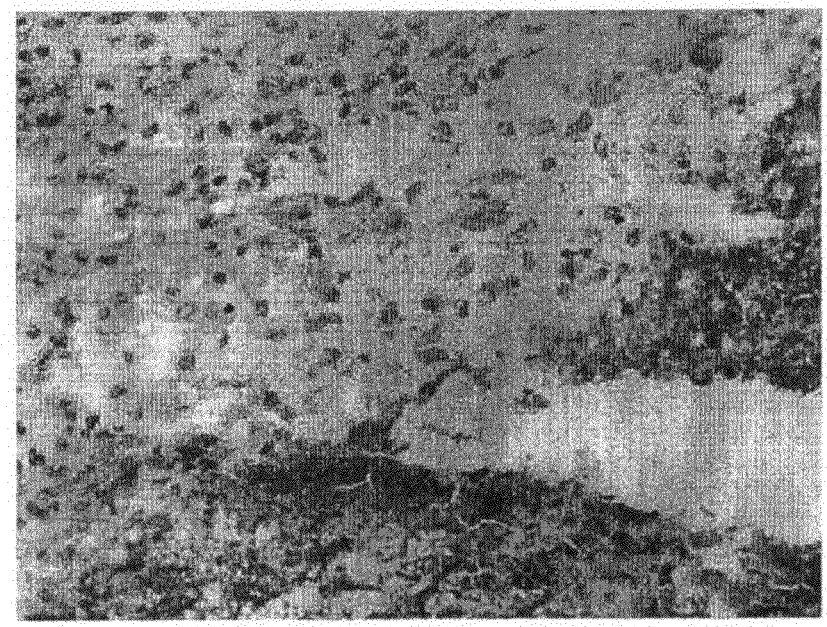

To demonstrate in vivo targeting of the EMD peptide, the MHC-HepIII complex or PBS (negative control) was injected into rats following myocardial injury. All surgical procedures were approved by the Committee for Animal Research of the University of California San Francisco (San Francisco, Calif.). The ischemia-reperfusion model used in this study has been extensively tested in our lab. Sprague-Dawley rats (225-250 g) were anesthetized with isoflurane. The chest was opened by a median sternotomy, and a single stitch of 7-0 Ticron suture (United States Surgical division of Tyco Healthcare, Norwalk, Conn.) was introduced around the left anterior descending (LAD) coronary artery and tightened to occlude for 25 min before reperfusing the vessel. The chest was then closed and the animal was allowed to recover. The rats were injected intravenously via the external jugular vein one day after the myocardial infarct (MI), and then sacrificed on Day 1, 2, 4, and 7 (N=1 per group). The hearts from each group were excised, fresh frozen, and sectioned into 10 slices. The presence of the MHC-HepIII complex in the infarct region was determined by immunostaining the heart sections using a Mouse on RAT HRP (Horse Radish Peroxidase) Polymer Kit (Biocare Medical, Concord, Calif.). The kit stains for any primary rat antibody that was grown in mouse, as was the case for the anti-MHC. Positive staining (brown) is seen only in the infarct zone for the heart treated with MHC-HepIII (FIG. 4). Thus, the Hep III EMD peptide was successfully conjugated to an injury associated antigen specific binding component (anti MHC antibody) and targeted to an injured tissue (the MI region).

Example 5

In Vivo Administration of a Targeted EMD Peptide for the Repair of Injured Myocardial Tissue This example demonstrates that the targeted EMD peptide facilitates the repair and/or regeneration of an injured tissue. The tissue injury was induced using the same procedure as described above in Example 4.

Following the MI and prior to the injection of the targeted EMD peptide, the rats were randomized to either control (PBS) or treatment groups (MHC-HepIII, or MHC only). Each animal received a single injection 500 μl (~100 μg of total protein) via the external jugular vein using a 30 gauge needle 1-2 days after MI. The rats were sacrificed 5-6 weeks post treatment.

Immediately after sacrifice, the heart was removed, rinsed in ice-cold saline, blotted-dry and fresh frozen in Tissue Tek O.C.T. freezing medium (Sakura Finetck, Torrance, Calif.), and sectioned into 10 μm slices. Representative slides were stained with Masson's trichrome stain for determination of infarct size.

Angiogenesis in the infarct was examined by immunohistochemical staining with mouse monoclonal anti-CD31 (BD Biosciences Pharmingen, San Diego, Calif.) to visualize capillaries and with mouse monoclonal anti-SMA (Sigma, St. Louis, Mo.) to detect arterioles and myofibroblasts. The staining assay was performed with using Mouse-on-rat HRP-polymer (Biocare Medical, Concord, Calif.), with pretreatment with peroxidase and Background Sniper blocking agents. Capillaries in the infarct were identified as a single layer of CD31-positive cells with flattened morphology. Vessel density was calculated on the basis of five high magnification fields per section that spanned the entire infarct and averaged among five sections for each sample. Arterioles within or bordering the infarct were identified as staining positive for SMA and as having a visible lumen with a diameter between 10 and 100 μm. Arteriole density was calculated as the average number of arterioles in the total infarct area, out of five representative slides per sample.

Figure 5:
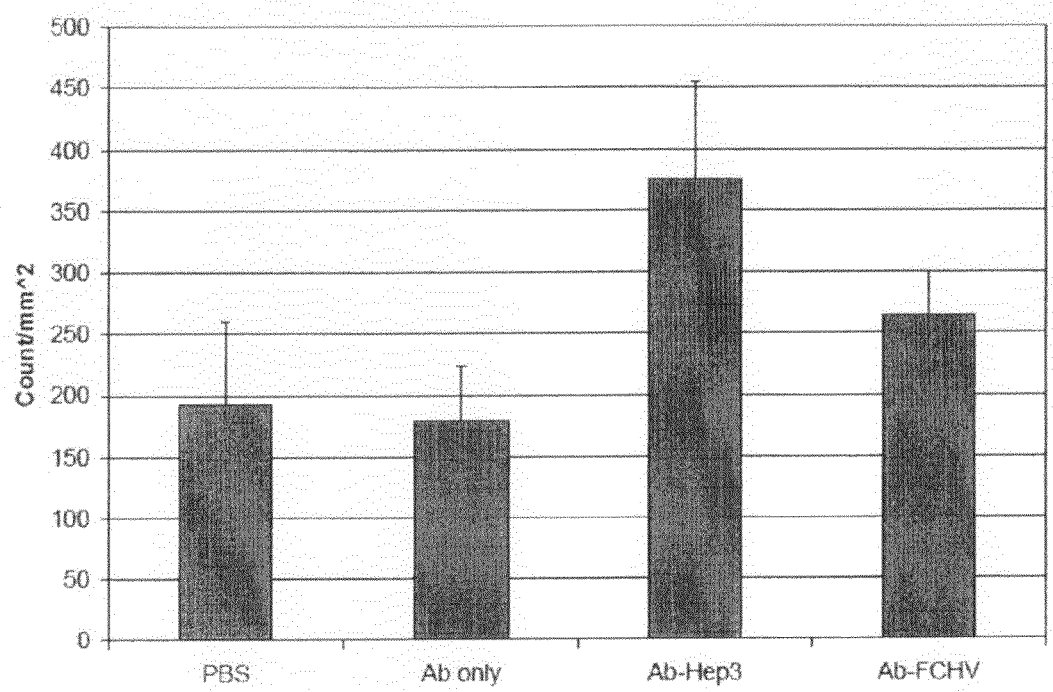
FIG. 5 shows the ability of the targeted Hep III EMD peptide to induce angiogenesis in injured myocardial tissue compared to antibody alone, or PBS control. The results demonstrate that the targeted Hep III peptide and the targeted FCHV peptide exhibit an angiogenic property when targeted to an injured myocardial tissue in vivo as compared to the PBS control at ($p<0.05$).

The results as shown in FIG. 5, indicate that MHC-HepIII (p=0.0028) and MHC-FC/HV (p=0.044) showed a statistically significant increase in angiogenesis compared to animals treated with PBS (control) at the p<0.05 level. Therefore, we have successfully demonstrated that the EMD peptide HepIII targeted to the site of a myocardial infarct aids in the repair and regeneration of the injured tissue.

All patents, patent applications, sequences, sequence accession numbers, and other publications cited in this application are hereby incorporated by reference in their entirety for all purposes.

What is claimed is:

1. A composition for repair of an injured tissue, the composition comprising
an injury-associated antigen-specific binding component conjugated to an extracellular matrix derived (EMD) peptide,
wherein the injury-associated antigen-specific binding component is an antibody that specifically binds myosin heavy chain and
wherein the EMD peptide comprises a Hep III peptide comprising the sequence of SEQ ID NO:2, and exhibits the ability to: (i) activate cells; (ii) attach cells; and (iii) exhibits a chemotropic property.

2. The composition of claim 1, wherein the EMD peptide further exhibits an angiogenic property.

3. The composition of claim 1, wherein the injury-associated antigen-specific binding component and the EMD peptide are chemically or recombinantly conjugated.

4. The composition of claim 1, wherein the antibody is selected from the group consisting of a (Fab)'2 fragment, an ScFv, a human antibody, and a humanized antibody.

5. The composition of claim 1, further comprising a pharmaceutically acceptable excipient.

* * * * *